United States Patent
Burr et al.

(10) Patent No.: US 9,301,796 B2
(45) Date of Patent: Apr. 5, 2016

(54) CRYOSURGERY SYSTEM

(75) Inventors: Ron Burr, Parkton, MD (US); Janel Petrilli, Pittsburgh, PA (US)

(73) Assignee: CSA MEDICAL, INC., Baltimore, MD (US)

( * ) Notice: Subject to any disclaimer, the term of this patent is extended or adjusted under 35 U.S.C. 154(b) by 634 days.

(21) Appl. No.: 13/411,395

(22) Filed: Mar. 2, 2012

(65) Prior Publication Data

US 2013/0231651 A1 Sep. 5, 2013

(51) Int. Cl.
*A61B 18/02* (2006.01)
*A61B 17/00* (2006.01)
*A61B 18/00* (2006.01)
*A61B 19/00* (2006.01)

(52) U.S. Cl.
CPC ... *A61B 18/0218* (2013.01); *A61B 2017/00973* (2013.01); *A61B 2018/00041* (2013.01); *A61B 2018/00642* (2013.01); *A61B 2018/0212* (2013.01); *A61B 2019/448* (2013.01); *A61B 2019/464* (2013.01); *A61B 2218/007* (2013.01)

(58) Field of Classification Search
USPC .................................................. 606/20–21
See application file for complete search history.

(56) References Cited

U.S. PATENT DOCUMENTS

| | | | |
|---|---|---|---|
| 3,782,386 A | 1/1974 | Barger et al. | |
| 4,146,030 A | 3/1979 | Holroyd | |
| 6,287,304 B1 * | 9/2001 | Eggers et al. | 606/37 |
| 6,887,234 B2 | 5/2005 | Abboud et al. | |
| 7,331,948 B2 * | 2/2008 | Skarda | 604/527 |
| 7,507,233 B2 | 3/2009 | Littrup et al. | |
| 2007/0233055 A1 * | 10/2007 | Abboud et al. | 606/22 |
| 2009/0157002 A1 * | 6/2009 | Dumot et al. | 604/131 |
| 2010/0057067 A1 | 3/2010 | Baust et al. | |
| 2011/0144524 A1 | 6/2011 | Fish et al. | |

OTHER PUBLICATIONS

International Search Report issued on Nov. 22, 2013 in corresponding International Application No. PCT/US2013/028935.

* cited by examiner

*Primary Examiner* — Paula J Stice
(74) *Attorney, Agent, or Firm* — Kacvinsky Daisak Bluni PLLC

(57) ABSTRACT

An improved cryosurgical system for application of medical-grade liquid nitrogen to a treatment area via a small, low pressure, open tipped catheter. The system includes a console, including a touch panel computer, a cryogen module, a suction module and an electronics module, all packaged in a mobile cart, and a disposable spray kit. Improved features include optional low cryogen flow setting to reduce the cryogen flow rate by 50%, improved cryogen flow consistency reducing pressure pulses and peaks (improved sensors, control systems, and control algorithms), an integrated suction pump for improved consistency and self-checks, specified vent tube areas and corresponding maximum expected pressures during cryospray procedure; optional pressure sensing capability to monitor pressure during a treatment, and improved catheter design.

9 Claims, 10 Drawing Sheets

| | Round Vent Area | Annular Vent Area |
|---|---|---|
| Diagram of Vent Shape | ← → Vent Tube ID | ← → Vent Tube ID / Annulus / Scope OD |
| Vent Area Calculation | Area ~ 3/4 * $d_{tube}^2$ | Annulus = ½ ($d_{tube}$ - $d_{scope}$) <br> Area ~ 3 * $d_{tube}$ * annulus |

Diagram of Venting Tube Area (d=diameter)

FIG. 7

| Vent Tube ID (mm) | Vent Area (mm²) | Max Pressure (cmH2O) | |
|---|---|---|---|
| | | Low Flow | Normal Flow |
| 3.2 | 8 | 35 | 95 |
| 5.0 | 20 | 15 | 25 |
| 6.0 | 29 | <15 | <25 |
| 7.0 | 38 | <15 | <25 |

Round Vent Area Calculation and Maximum Expected Pressure during 20sec Cryogen

FIG. 8

| Vent Tube ID (mm) | Scope Outer Diameter (mm) | | | | |
|---|---|---|---|---|---|
| | 6 | 7 | 8 | 9 | 10 |
| 8.0 | 22 | | | | |
| 8.5 | 29 | | | | |
| 9.0 | 35 | 25 | | | |
| 9.5 | 43 | 32 | | | |
| 10.0 | 50 | 40 | 28 | | |
| 10.5 | 58 | 48 | 36 | | |
| 11.0 | 67 | 57 | 45 | 31 | |
| 11.5 | 76 | 65 | 54 | 40 | |
| 12.0 | 84 | 75 | 63 | 50 | 35 |
| 12.5 | 94 | 84 | 72 | 59 | 44 |

Annular Vent Area Calculation (mm$^2$)

FIG. 9

| Vent Area (mm$^2$) | Max Pressures (cmH2O) | |
|---|---|---|
| | Low Flow | Normal Flow |
| 6 | 60 | 125 |
| 20 | 25 | 40 |

Annular Vent Area Maximum Expected Pressure during 20sec Crygen

FIG. 10

Lumped Parameter Schematic for Cryospray System Tuning and Control

CRYOSURGERY SYSTEM

BACKGROUND

1. Field of the Invention

The present invention relates generally to cryosurgery systems, and more particularly, to an advanced cryosurgery system having improved cryogen flow and flow control, an integrated suction pump, a body cavity pressure sensor and an improved delivery catheter.

2. Related Art

A variety of medical conditions may be treated by ablation of tissue within the body. Tissue ablation refers to the removal or destruction of tissue, or of tissue functions. Traditionally, invasive surgical procedures were required to perform tissue ablation. These surgical procedures required the cutting and/or destruction of tissue positioned between the exterior of the body and the site where the ablation treatment was conducted, referred to as the treatment site. Such conventional surgical procedures were slow, costly, high risk, and resulted in a long recovery time.

Cryoablation is a relatively new procedure in which tissue ablation is conducted by freezing diseased, damaged or otherwise unwanted tissue (collectively referred to herein as "target tissue"). Appropriate target tissue may include, for example, cancerous or precancerous lesions, tumors (malignant or benign), fibroses and any other healthy or diseased tissue for which cryoablation is desired.

Cryoablation may be performed by using a system that sprays low pressure cryogen on the target tissue. Such systems are referred to as cryosurgery spray systems, or simply, cryosurgery systems, herein. As used herein, cryogen refers to any fluid (e.g., gas, liquefied gas or other fluid known to one of ordinary skill in the art) that has a sufficiently low boiling point to allow for therapeutically effective cryotherapy and is otherwise suitable for cryogenic surgical procedures. For example, acceptable fluids may have a boiling point below approximately negative (−) 150° C. The cryogen may be nitrogen, as it is readily available. Other fluids such as argon and air may also be used.

During operation of a cryosurgery system, a clinician, physician, surgeon, technician, or other operator, (collectively referred to as "operator" herein) sprays cryogen on the target tissue via a delivery catheter. The spray of cryogen causes the target tissue to freeze or "cyrofrost." This freezing of the tissue often causes the target tissue to acquire a white color (indicative of cryofrost). The white color indicates that the target tissue freezing has inititated. The physician may visually monitor and/or time additional cryospray duration in order to control the depth of injury. The temperature range for cryofrost can be approximately negative (−) 10° C. to approximately negative (−) 75° C. However, the particular temperature for cryofrost will depend on the target tissue, including size, location, etc. The time period to reach cryofrost may vary, from approximately 5 seconds to approximately 2 minutes or more depending on the size and location of the target tissue and the thermodynamic potential of the cryogen. A cryosurgery system may include a camera system that enables the operator to monitor the cryogen delivery and determine when cyrofost has occurred.

SUMMARY OF THE INVENTION

According to one aspect of the present invention, there is provided an advanced cryosurgery system having improved cryogen flow and flow control, an integrated suction pump, a pressure sensor and an improved delivery catheter.

Embodiments of the present invention are directed to a cryosurgery system having a cryogen delivery apparatus. In accordance with embodiments of the present invention, the cryosurgery system may further include a cryogen source configured to provide the cryogen to the cryogen delivery apparatus, a regulation apparatus fluidically coupled to the cryogen source and to the cryogen delivery apparatus, and a controller communicatively coupled to the regulation apparatus configured to control the release of cryogen into the cryogen delivery apparatus. Exemplary cryosurgery systems in which the present invention may be implemented include, but are not limited to, those systems described in commonly owned U.S. Pat. Nos. 7,255,693, 7,025,762, 6,383,181, and 6,027,499 and U.S. patent application Ser. Nos. 11/956,890 and 12/022,013, the entirety of which are each hereby incorporated by reference herein. Embodiments of the present invention are described below in connection with one embodiment of such exemplary cryosurgery system shown in FIG. 1.

The improved system of the present invention is a cryosurgical tool that applies a medical-grade liquid nitrogen spray to the treatment area via a small, low pressure, open tipped catheter. The improved system of the present invention comprises (1) a console, including a touch panel computer, a cryogen module, a suction module and an electronics module, all packaged in a mobile cart, and (2) a disposable spray kit.

Users interact with the console through a dual foot pedal and the touch panel. A processor/controller and associated software manage the cryogen level sensing, filling, pressure, cooling, defrost, suction, timing and data management functions. A wireless remote control provides alternative timer control from a distance in the treatment room. A fill kit, stored on the rear of the console, in conjunction with software controls, allows for semi-automatic liquid nitrogen transfer from the source tank to the console. Safety features include sensors, indicators, tank pressure relief valves, an isolated low voltage power system, and an emergency button to be used in the event of user or technical malfunction. The mechanical cart is easily maneuvered and has on-board storage built into the panels for the foot pedals, instructional material (e.g. operator manual), disposables (e.g., spray kits), remote control and fill kit. The modular design of the console allows for easy manufacturability and serviceability.

The spray kit of the present invention consists of a sterile, single-use catheter of improved construction, a cryogen decompression tube, and pre-cut accessory suction tubes. The catheter is flexible and capable of retroflex in a scope. The cryogen decompression tube and accessory tubes are included for use with the on-board suction system.

In particular, several key new features have been added to improve cryogen flow/delivery and gas venting:

- optional low cryogen flow setting to reduce the cryogen flow rate by 50%,
- improved cryogen flow consistency reducing pressure pulses and peaks (improved sensors, control systems, and control algorithms),
- an integrated suction pump for improved consistency and self-checks,
- specified vent tube areas and corresponding maximum expected pressures during cryospray procedure;
- optional pressure sensing capability to monitor body cavity pressure during a treatment, and
- improved, retroflex-capable catheter design.

As a result of the new cryogen delivery features, the cryogen flow is more consistent and the pressure pulsing has been reduced to create a more efficient cryogen flow which generates less pressure in the body. As a result of the new gas venting features, the active suction is more consistent and has additional settings and warnings to provide greater flexibility to the physician. The addition of passive venting instructions provides information regarding cryogen flow and vent area so that the physician can make an informed decision on the appropriate combinations to limit pressure build-up within a body cavity. In addition, an optional pressure sensing capability is available to monitor pressure during a treatment.

BRIEF DESCRIPTION OF THE DRAWINGS

Embodiments of the present invention will be described in conjunction with the accompanying drawings, in which:

FIG. 7 is a diagram of venting tube area;

FIG. 8 shows round vent area calculation and maximum expected pressure during 20 sec cryosurgery.

FIG. 9 shows annular vent area calculation.

FIG. 10 shows annular vent area maximum expected pressure during 20 sec. cryosurgery.

DETAILED DESCRIPTION OF THE PREFERRED EMBODIMENTS

Figure 1:
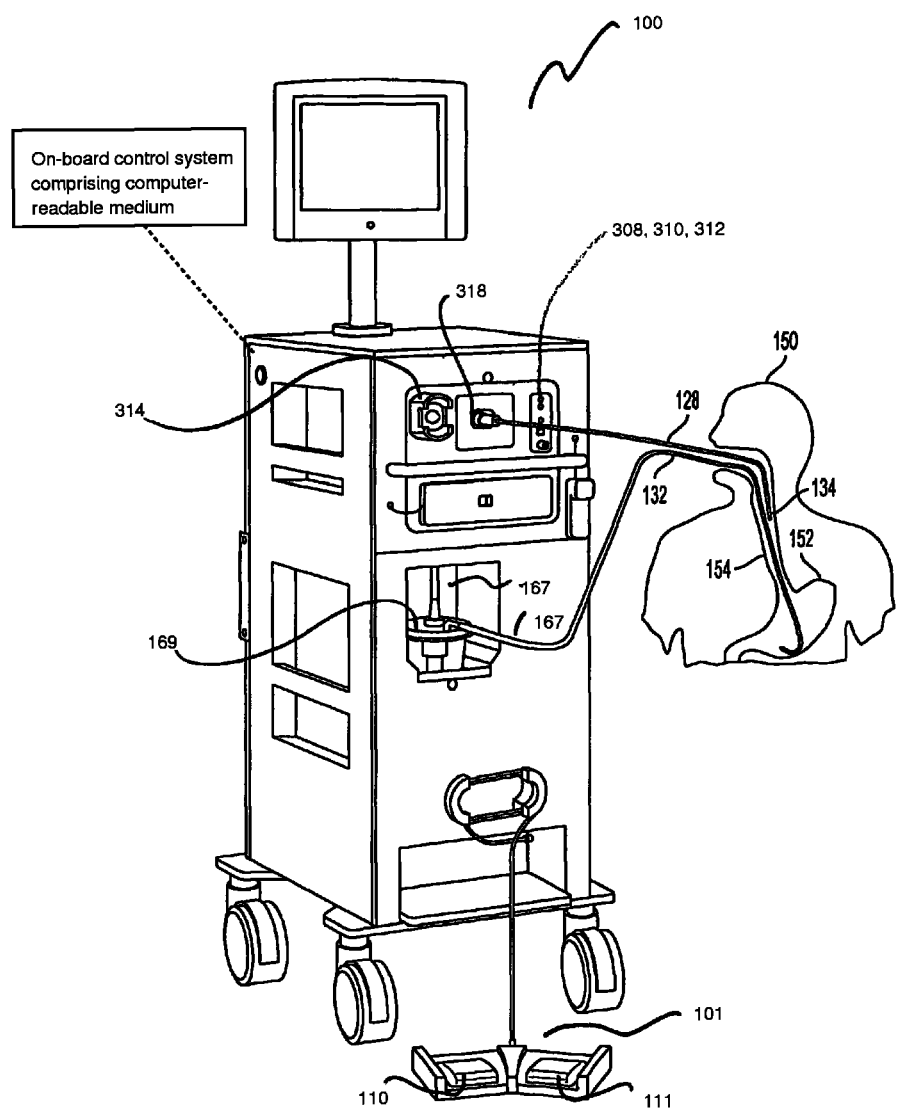
FIG. 1 is a perspective view of a cryosurgery system according to an embodiment of the invention.
Figure 2:
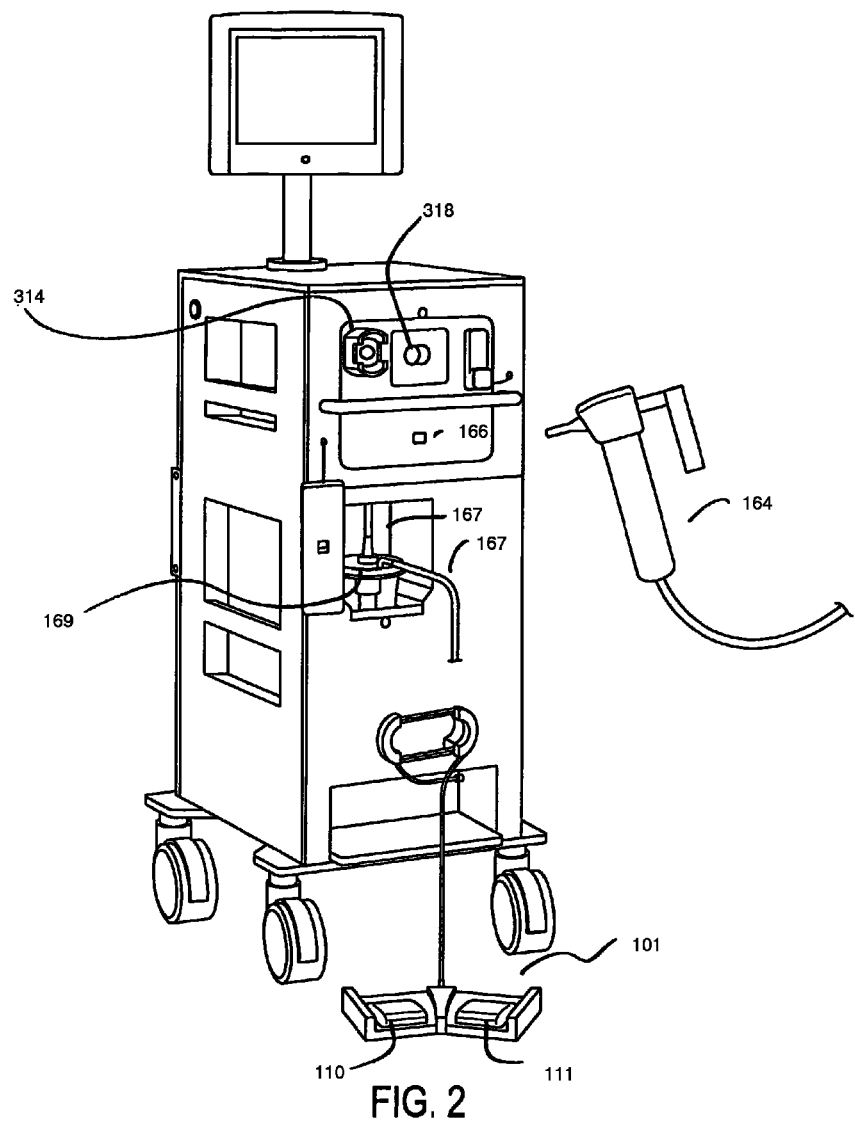
FIG. 2 is a perspective view of another embodiment of a cryosurgery system according to an embodiment of the invention.
Figure 3:
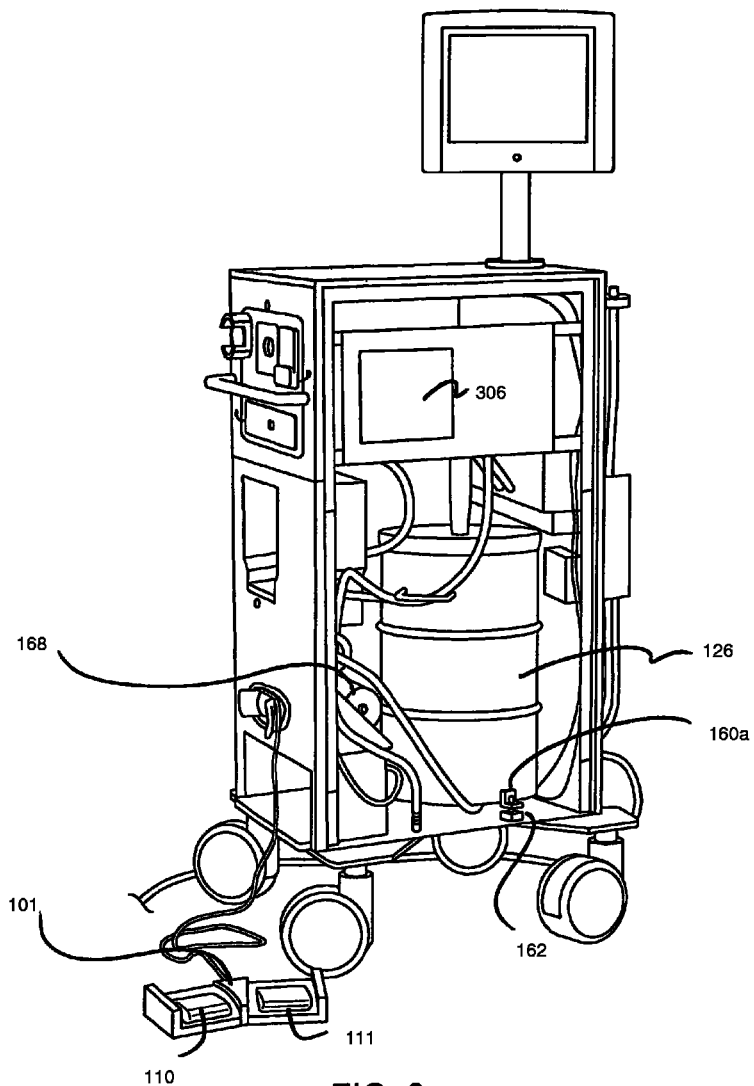
FIG. 3 is a perspective view of the interior of an embodiment of a cryosurgery system according to an embodiment of the invention.

A simplified perspective view of an exemplary cryosurgery system in which embodiments of the present invention may be implemented is illustrated in FIGS. 1-3. Cryosurgery system 100 comprises a pressurized cryogen storage tank 126 to store cryogen under pressure. In the following description, the cryogen stored in tank 126 is liquid nitrogen although cryogen may be other materials as described in detail below. The pressure for the liquefied gas in the tank may range from 5 psi to 50 psi. According to a more preferred embodiment, pressuring in the tank during storage is 40 psi or less, and pressure in the tank during operation is 35 psi or less. According to a more preferred embodiment, pressure in the tank during storage is 35 psi or less and pressuring during operation is 25 psi or less. According to a most preferred embodiment, pressure during operation at normal nitrogen flow is 22±2 psi, and pressure during operation at low nitrogen flow is 14±2 psi. When the pressure in the tank during operation is set to 22 psi, the flow rate/cooling capacity of the nitrogen is 25 W. When the pressure in the tank during operation is set to 14 psi, the flow rate/cooling capacity of the nitrogen is 12.5 W.

Level and Fill

Liquid nitrogen (LN2) resides on the bottom of the tank and liquid nitrogen gas/vapor (GN2) occupies the top portion of the tank. The tank is supported at 3 points 160a, 160b, 160c; see FIGS. 3 and 4. The tank level is measured with a precision load cell 162 under a flange built into the front mount of the cryogen tank and acting of one of the three support points. The load cell senses the ⅓ of the weight of the tank. A signal conditioner amplifies signal for input to an analog input channel of the controller, which is read by the software and used to determine/display the actual tank level. This improved system provides greater reliability and precision for monitoring the tank level.

The console of the present invention comes with an insulated quick release custom fill hose 164 to fill the tank through the external fill port 166 in a semi-automatic cryogen fill process. A fill port switch 168 on the console actuates only when the fill hose is in the locked position. During the fill process, liquid nitrogen passes through a filter 170 and transfer valve 172 en route to the tank; see FIG. 5. The software automatically shuts off the electronic transfer valve 172 when the tank is full and vents the hose prior to removing from the console.

Pressure

The improved system of the present invention utilizes valves and a pressure transducer to continuously monitor and control the pressure of liquid nitrogen in the tank during use. The console monitors the current pressure of the tank via a pressure transducer 174. The software reads the current pressure from the transducer and adjusts the pressure accordingly. If pressure is too low, the software actuates the pressure build circuit valve 176 to increase the pressure to a specified threshold and then turns off. When the pressure is too high, the software turns on the vent valve 178 until the pressure reaches a specified threshold. The system allows two user selectable pressure levels (corresponding to two nitrogen flow rates), normal (22±2 psi/25 W) and low (14±2 psi/12.5 W). The console of the present invention has a redundant pressure switch 180 designed to confirm and ensure accurate tank pressure readings.

A mechanical relief valve 182 on the console tank ensures that the tank pressure stays in a safe pressure range. Due to the improved and constant pressure monitoring and adjustment the set point on the mechanical relief valve was adjusted from 50 psi to 35 psi, allowing for a lower tank storage pressure. A redundant burst disk 184 provides protection should the mechanical relief valve fail. For optimal safety, both electronic and mechanical pressure valves are present to regulate the pressure, providing triple redundancy in the event of failure. In addition, a redundant pressure switch was designed into the system to provide accurate tank pressure readings and is checked during the built-in-test (BIT).

Thermal Cooling

The improved system of the present invention utilizes a manifold assembly comprised of a cryogen valve 186, catheter valve 188, and defrost valve 190 to control liquid nitrogen delivered through the catheter. When the cryogen valve 186 is actuated, liquid nitrogen exits the tank through the lance 194 and proceeds through the manifold assembly 196 where an orifice is present to allow gas to exit the line through a vent 192 or other fixed orifice and cool down the internal cryogen circuit. During this precool, the catheter valve 188 downstream of the manifold remains closed. A data acquisition board collects data from a thermocouple located under the manifold. In the precool function, the system software monitors data from the thermocouple, and opens the cryogen valve to cool the manifold when its temperature is above the desired set-point.

Depressing the cryogen foot pedal 110 opens both the cryogen valve 186 and catheter valve 188 allowing liquid nitrogen to flow into the catheter 128; releasing the pedal stops the flow of cryogen (momentary action). The software set-up screen provides two user selectable cooling levels of cryogen flow, normal and low, described above. Nominal cooling performance at normal and low flow is 25 W and 12 W, respectively.

Low cryogen flow generates considerably less pressure rise with the same venting area and allows treatment with more precise control. The precooling process has been automated on the console of the present invention where the prior art console requires the physician to manually spray prior to inserting into the scope. Automated precool with internal circulation (improved over manual flow through catheter) allows improved ease of use and maximizes cooling consistency and minimizes gas discharged into patient.

In the embodiment illustrated in FIG. 1, a conventional therapeutic endoscope 134 is used to deliver the nitrogen gas to target tissue within the patient. Endoscope 134 may be of any size, although a smaller diagnostic endoscope is preferably used from the standpoint of patient comfort. In certain embodiments, a specially designed endoscope having a camera integrated therein may also be used. As is known, an image received at the lens on the distal end of the camera integrated into endoscope 134 may be transferred via fiber optics to a monitoring camera which sends video signals via a cable to the a conventional monitor or microscope, where the procedure can be visualized. By virtue of this visualization, the surgeon is able to perform the cryosurgery at treatment site 154.

As the liquid nitrogen travels from tank 126 to the proximal end of cryogen delivery catheter 128, the liquid is warmed and starts to boil, resulting in cool gas emerging from the distal end or tip of catheter 128. The amount of boiling in catheter 128 depends on the mass and thermal capacity of catheter 128. Since catheter 128 is of small diameter and mass, the amount of boiling is not great. (The catheter would preferably be "French Seven".) When the liquid nitrogen undergoes phase change from liquid to gaseous nitrogen, additional pressure is created throughout the length of catheter 128. This is especially true at the solenoid/catheter junction, where the diameter of the supply tube relative to the lumen of catheter 128 decreases from approximately 0.5 inches to approximately 0.062 inches, respectively.

When the liquid nitrogen reaches the distal end of catheter 128 it is sprayed out of cryogen delivery catheter 128 onto the target tissue. It should be appreciated that certain embodiments the cryosurgery system may be able to sufficiently freeze the target tissue without actual liquid nitrogen being sprayed from catheter 128. In particular, a spray of liquid may not be needed if cold nitrogen gas is capable of freezing the target tissue.

Freezing of the target tissue is apparent to the physician by the acquisition of a white color, referred to as cryofrost, by the target tissue. The white color, resulting from surface frost, indicates the onset of mucosal freezing sufficient to initiate destruction of the diseased tissue. The operator may use the system timer to freeze for a specified duration once initial cryofrost is achieved in order to control the depth of injury. In one embodiment, the composition of catheter 128 or the degree of insulating capacity thereof will be selected so as to allow the freezing of the mucosal tissue to be slow enough to allow the physician to observe the degree of freezing and to stop the spray as soon as the surface achieves the desired whiteness of color. The operator may monitor the target tissue to determine when cryofrost has occurred via the camera integrated into endoscope 134. The operator manipulates cryogen catheter 128 to freeze the target tissue. Once the operation is complete, cryodecompression tube 132, catheter 128, and endoscope 134 are withdrawn.

Figure 11:
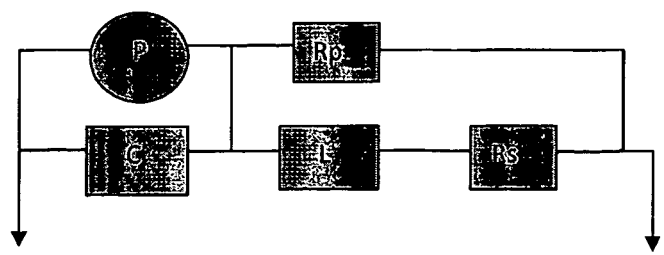
FIG. 11 shows schematic diagram of cryogen flow path and fluidic tuning and control to achieve consistent and stable flow and cooling.
Figure 12:
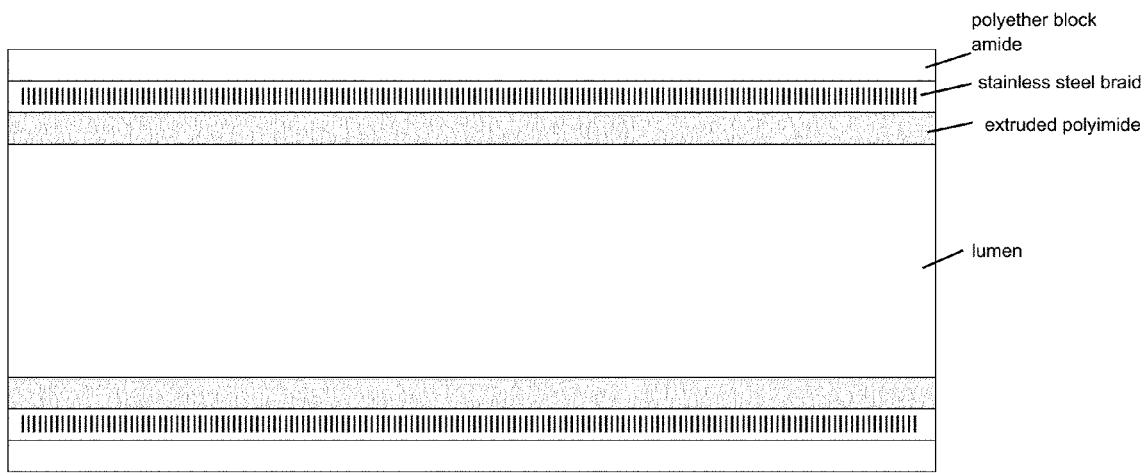
FIG. 12 is a representation of a cryosurgical catheter according to an embodiment of the invention.

Proper design and matching of cryogen storage and control components allows for stable and well-controlled cryogen flow. The dynamic behavior of the system can be simply visualized by the lumped parameter model of FIG. 11, where P represents the pressure in the tank; $R_p$ represents "parallel resistance" which models the resistance of the vent orifice 192; C represents the fluid compliance capacity (i.e., the compressibility or "springiness" of the liquid and gas in the tank 126, together with the tank level head height); $R_s$ represents the series resistance, or the length and inside diameter of the catheter; and I represents Inductance, or the weight of the long narrow fluid column in the catheter. The inventors have discovered a critical intersection of these values that provides an ideal and critically damped response to the cryogen and subsequent gas flow/pressure allowing dramatically improved smoothness and consistency of cryogen delivery to the target tissue as compared to the prior art, as set forth below.

Catheter length may be anywhere from 10 inches to 100 inches. Inside diameter of the catheter may be anywhere from 1 mm to 4 mm. The tank size may be anywhere from 5 L to 100 L; its diameter may range from 4 inches to 36 inches. The vent orifice of the manifold may be 0.01 inches to 0.1 inches. The inventors have discovered that the following critical combination of dimensions provides a surprisingly improved smoothness and consistency of cryogen delivery: catheter length: 84 inches±9 inches; catheter inside diameter: 2 mm±0.2 mm; tank size: 15 L±1.5 L; tank diameter: 14 inches±1.5 inches; manifold vent orifice: 0.05 inches±0.005.

Active feedback control via pressure, resistance or bypass control and also be incorporated to aid in ideal tuning and response.

Thermal Defrost

The defrost function is useful for thawing the catheter after cryogen spray, before removal from the scope. A defrost circuit directs gaseous nitrogen from the top of the tank through a heater 191 and defrost valve 190 to the catheter 128. When the defrost button on the software screen is pressed, the defrost circuit is activated for a prescribed time (e.g. 30 seconds) but can be stopped earlier at the user's discretion. A low voltage (24VDC) DC defrost heater delivers 6 W minimum of warming/defrost performance but minimizes variation due to line voltage and limits maximum gas temperature, as compared to the prior art line voltage (120V) AC heater.

Figure 6:
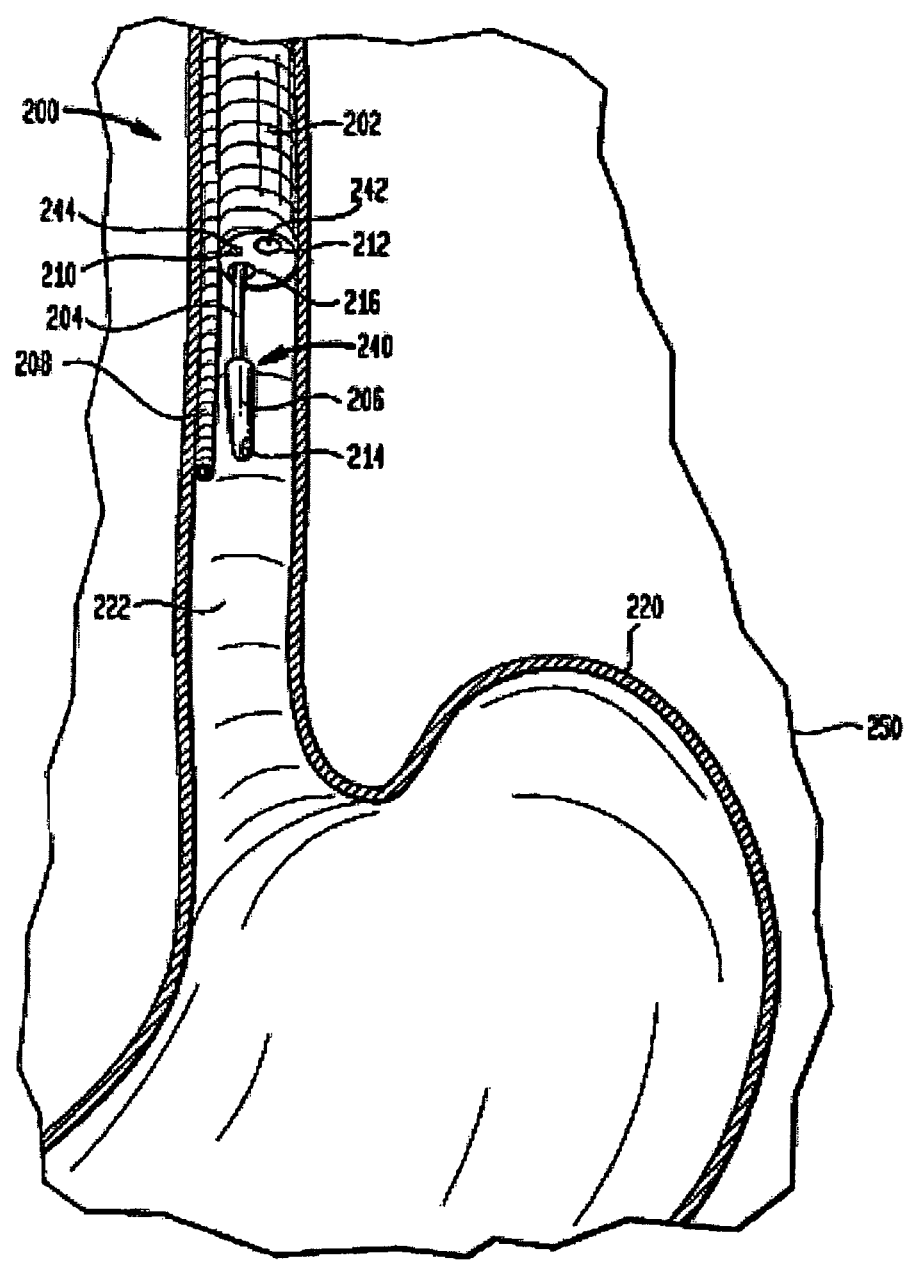
FIG. 6 is a perspective view of a crysurgery delivery system according to an embodiment of the invention.

FIG. 6 is a perspective view of a portion of a cryosurgery system 200 having a cryogen delivery apparatus 240. Cryosurgery system 200 comprises an endoscope 202 having lumens 210, 212 and 216 therein. As shown, endoscope 200 may be positioned in the esophagus 222 of patient 250. Lumen 212, disposed in endoscope 202, is configured to receive an endoscope camera 242. An image received at the lens of endoscope camera 242 may be transferred via fiber optics to a monitoring camera. The monitoring camera then sends video signals via a cable to a conventional monitor or microscope, where the image captured by the lens can be visualized. As shown in FIG. 6, endoscope camera 242 may be inserted through lumen 212 to allow an operator to view the cryosurgery procedure. Lumen 210 is configured to have disposed therein a light 244 that is configured to illuminate the treatment site.

Lumen 216 is configured to receive cryogen delivery apparatus 240. Cryogen delivery apparatus 240 comprises a retroflex-capable cryogen delivery catheter 204, catheter tip 206, and one or more holes 214. After insertion of the cryogen delivery apparatus into the patient, cryogen is provided to cryogen delivery catheter 204 from a cryogen source. Tip 206 causes the cryogen to be sprayed on the target tissue via hole 214. A dual lumen (for both passive and active venting) cryo-decompression tube 208 is provided to evacuate the treatment area of undesirable gases, particles, fluids etc.

Treatment site 154 as depicted in FIG. 1 is the esophagus of patient 150. It should be appreciated, however, that the treatment site but may be any location within patient 150 such as inside stomach 152 or other cavities, crevices, vessels, etc. Since freezing is accomplished by boiling liquid nitrogen, large volumes of this gas are generated. This gas must be allowed to escape. The local pressure will be higher than atmospheric pressure since the gas cannot easily flow out of the treatment site such as the gastrointestinal tract. In the illustrated embodiment, nitrogen gas will tend to enter stomach 152, which has a junction with the esophagus (the esophageal sphincter) immediately adjacent to treatment site 154. In this case, without adequate or quick suction, stomach 152 of patient 150 may become distended and become uncomfortable for patient 150. This buildup of gas could also potentially cause stomach 152 or its lining to become damaged or torn. As such, to prevent this buildup of gas in stomach 152, a suction tube 132 (e.g., a nasogastric tube) as described hereinafter may be inserted into the patient to evacuate cryogen and other gases, particles, liquids, etc. from the patient.

Passive Venting

Passive venting is a method in which gas disperses from the treatment area by flow through either a natural or artificial orifice/lumen without suction. The instructions for use provide physicians with information on passive venting (cryogen flow, vent area, vent shape, see FIGS. 3-6) to limit pressure build-up in the body cavity. The area through which gas vents passively must be adequate to ensure excessive distention does not occur (e.g. 20 mm$^2$ at normal flow and 10 mm$^2$ at low flow). An optional (auxiliary) pressure sensing capability is built-in to aid the user in monitoring cavity pressure, if desired in either the active or passive venting modes.

The operating instructions allow physicians to determine the appropriate cryogen flow setting, vent area and vent shape (round, annular) to utilize passive venting. In addition, the smoother and more consistent cryogen spray allows for the reduction of pressure/pulsing by 50% at normal flow settings on the system of the present invention as compared to the prior art. With the low cryogen flow setting, the pressure is significantly reduced even further. Additionally, the console of the present invention has a pressure sense capability that can be used in conjunction with passive venting that allows the physicians to monitor cavity pressure during treatment.

Figure 4:
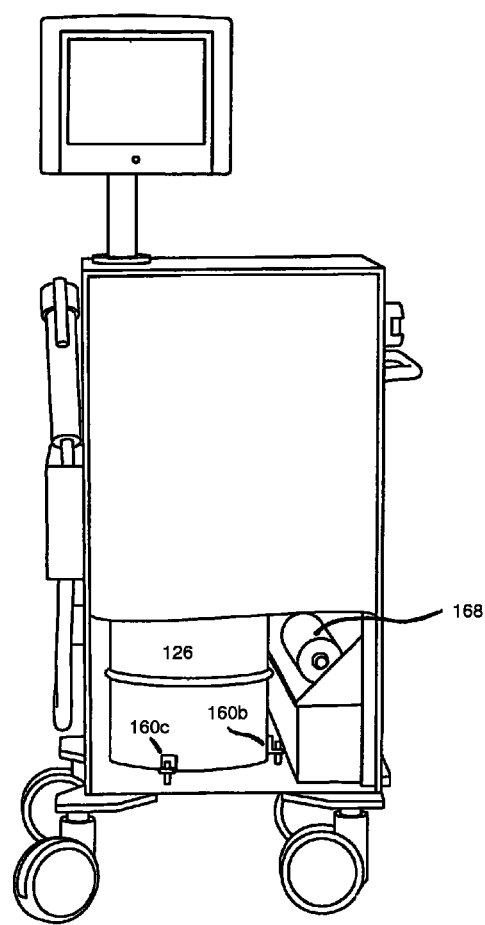
FIG. 4 is a perspective cutaway view of the reverse side of the embodiment of a cryosurgery system shown in FIG. 3.
Figure 5:
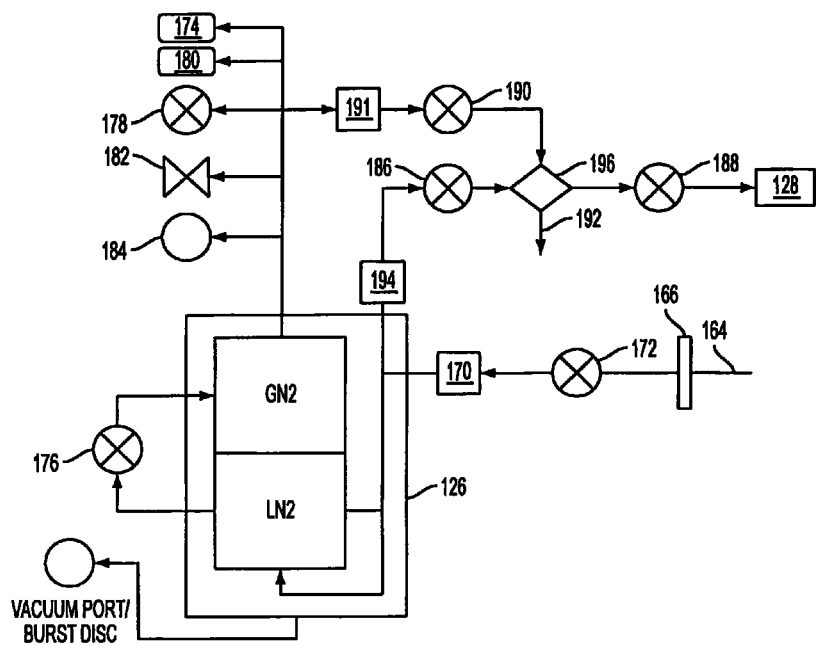
FIG. 5 is a schematic showing a cryogen storage, delivery and pressure control apparatus according to an embodiment of the invention.

The diameter of the area through which gas vents passively must be adequate to ensure distention does not occur. Passive venting may be used with a vent tube when spraying proximal to a resistor where the lumen is patent (open), or when the treatment area is open to atmospheric pressure (e.g., dermatological or open surgery). A lumen sizing device (e.g. stent sizer) may be used to measure the lumen to aid in selection of vent tube size. The greater the vent area, the lower the pressure. The vent tube can be a separate tube used strictly for venting gas and creates a round vent area. The vent tube can also provide an annular vent area where the scope passes through the center of the tube. FIG. 3 shows a comparison of annular and round vent area. FIGS. 4 and 5 show vent areas (mm$^2$) for different scope sizes and vent tube inner diameters (ID). The distal end of the passive venting tube should be placed in an unobstructed cavity near the procedure area if area is not sufficiently open to atmospheric pressure. If used, the proximal end of the passive venting tube should be positioned outside the body where the pressure is atmospheric.

FIGS. 4 and 6 show maximum expected pressures during a 20-second spray using round or annular vent shape, respectively.

Active Venting (Suction)

Active venting (suction) is the venting method in which the onboard suction is used to evacuate gas from the treatment area via the cryogen decompression tube 132. The suction is controlled by the physician through the use of a dual foot pedal (cryogen/suction) 101. Pressing the suction foot pedal 111 activates suction; pressing the suction foot pedal again de-activates suction (toggle action).

The on-board suction module is preferably mounted inside the lower front panel of the console. The suction control panel consists of a pump 168, control module, valve and sensor. The software set-up screen provides two user selectable levels of suction (normal, low). The front enclosure provides space for attaching a suction canister 169 and accessory tubing 167 One piece of pre-cut accessory tubing connects the suction canister to the console pump; another piece of pre-cut accessory tubing connects the suction canister to the decompression tubing. Electronic controls within the console verify adequate vacuum and allow the physician to control application of suction through the cryogen decompression tube using the foot pedal.

The prior art required the use of an external suction pump, while the console of the present invention has an integrated suction pump to improve overall consistency and provide control and self-checks. The present invention uses a normal vacuum setting to evacuate liquids that may accumulate in the treatment area or cryogen decompression tube in addition to removing the cryogen gas. The console of the present invention also has an additional, lower vacuum setting (50%) to allow the physician to pull less suction in certain situations (e.g., where flaccid lumen inhibits vision or movement). The integrated suction pump and sensor (32 lpm) improves consistency, suction flow, suction flexibility robustness relative to prior art external suction pump and gauge (25 lpm).

Spray Kit

The spray kit consists of a carton of five (5) sterile, single-use catheters with introducers in individual pouches and a carton of five (5) sterile, single-use CDTs with associated tubing in individual pouches. Each carton within a spray kit contains the instructions for use.

Improved Catheter

The catheter is designed to transport liquid nitrogen from the console to the patient treatment site. The catheter contains (1) a bayonet and hub for attachment to the console, (2) a layered polyimide and stainless steel braided shaft to minimize kinking and breaking, (3) insulation to protect the user from cold, (4) a strain relief to help prevent kinking when torqued by users and (5) an atraumatic tip to prevent damage to tissue. The laminated construction and braided material provides additional strength and flexibility, allowing the physician to retroflex the catheter during a treatment procedure, if needed. The catheter pouch contains an RFID tag that the user scans prior to use to prevent reuse and track disposable information. The catheter pouch also contains an introducer that provides reinforcement for the catheter and helps prevent kinking during use and when placing the catheter into the scope. The catheter is packaged in a protective tube to prevent damage during shipping.

The improved delivery catheter is comprised of three layers of flexible polyimide, surrounded by a stainless steel braid, which is in turn coated with an outer layer of PEBAX (polyether block amide). It was discovered that that extrusion of polyether block amide over the stainless steel braid allows the polyether block amide to wick through the pitch of the steel braid, helping to prevent kinking, breaking, or delamination during retroflex of the catheter. The polyether block amide also provides a desirable balance between hardness—important for smooth sliding of the catheter and general toughness, and softness, which is important for some degree of tackiness which allows the user to feel the movement of the catheter in the scope. The pitch of the stainless steel braid is configured to be fine enough to afford the required strength, not thick enough to allow the polyether block amide to wick through. The end of the catheter is provided with an atraumatic tip comprised only of polyether block amide, in the shape of a bullnose. This novel construction allows for retroflex of the catheter without kinking, breaking, or delamination of the catheter. For the purposes of this invention, retroflex is used to refer to the ability of a catheter to bend or turn approximately 180° about a radius of curvature of 1 inch or less. This is useful so that when the catheter is introduced into, for example, the stomach via the esophagus, the catheter can be turned approximately 180° in order to treat the roof of the stomach.

Cryogen Decompression Tube

The cryogen decompression tube 132 aids evacuation of nitrogen gas from the treatment site. The cryogen decompression tube connects via supplied accessory connection tubing 167 to a disposable suction canister 169 on the front of the console. The dual lumen cryogen decompression tube are coupled by ports that provide both active (to the suction pump) and passive (direct to ambient) vent paths.

Scan/RF'ID

Spray kit usage is tracked by scanning a Radio Frequency Identification (RFID) tag on the catheter packaging. The RFID reader 306 is mounted on the right side of the console. When a valid spray kit is detected, the associated indicators on the set up screen are updated and a three hour timer is started and constantly visible to the user for monitoring of procedure time.

Control/Electronics Panel

The control panel is located in the top upper section of the console and includes the following: auxiliary panel (pressure port 308, thermocouple input port 310 and digital input ports 312), emergency stop 314, USB port, catheter interface 318 and transfer interface, including external fill port 166. The catheter port on the console of the present invention has spring-loaded capture pins for improved robustness and improved tactical feel on insert and removal.

The electronics panel houses the compact data acquisition (cDAQ) controller, the level sense signal conditioner, the auxiliary pressure sensor, the interface board, the heater relay, the power supply and the power supply filter. The cDAQ controller contains removable DAQ modules that measure and output various signals and controls to and from the console. All signals and controls in the console are routed through an interface/interconnect board. The console of the present invention uses a universal medical grade power supply that powers all internal operations using 24 volts through the interface/interconnect board. Power from the 24VDC medical grade power supply is distributed to all console components through the interface board.

User Interface/Platform

The improved system of the present invention utilizes a graphical user interface (GUI) deployed on a touch panel. The software is comprised of six main application codes that govern operation of the system: Home, Fill, Test, Run (Procedure), Data and Service.

The Home module provides the central menu and access to the five application modules. Three (3) buttons located in the center of the Home screen allow access to the three main modules: Fill, Test and Run. Data and Service buttons are normally hidden; however, pressing the CSA logo makes them visible. Service is password protected allowing only authorized CSA personnel access. The module application codes are accessed by selecting the applicable button from the Home screen.

The Fill module implements a semi-automatic fill process that (1) verifies the fill hose is connected before proceeding, (2) controls applicable valves required for filling the tank, (3) displays the real time tank level and (4) automatically shuts off when the tank is full.

The console of the present invention includes a semi-automated fill process accessed from the front of the console that provides graphical information to monitor the fill process. The prior art is a manual process conducted at the rear of the console that does not include a visual display during fill.

The test module implements an automatic built-in test (BIT) when powering up the console or when selected by the user. The BIT checks each hardware module and verifies performance of the system prior to entering the procedure code (i.e., Run button). Upon completion, the BIT automatically returns to the Home module. If the BIT passes, the Run button is enabled for entrance into Run. If the BIT fails, a status indicator on the Home screen alerts the user of the required action and disables the Run button. The console of the present invention allows the user to view both quantitative and pass/fail results for each test as they are completed as well as an overall result.

The procedure application module (Run button) controls the thermal, timing and suction functions and is used during the treatment of patients. When the Run button is pressed, the user can select from a set-up screen or a run screen. The set-up screen monitors key system parameters (scan, tank level, pressure, and thermal) with color coded text indicators to indicate operating states (green ready, red not ready). The set-up screen also contains controls for selecting cryogen flow (normal/low), suction (normal/low), and sound volume (normal/low). The run screen provides inputs to set and control the timer, precool and defrost. The run screen also provides color coded procedure, suction state/warning indicators and auxiliary pressure indicators.

The console of the present invention has optional lower cryogen flow and suction setting. The system of the present invention displays additional information regarding the system status (e.g., tank level, tank pressure, precool, cryogen state, suction/venting state).

The Data module provides the ability for the user to view and download log files through a drop down menu. There are a total of six (6) logs that are visible to the user (fill, test, procedure, system, error, and service) to view relevant details. Log files may be downloaded to a USB drive for off-line viewing and aid in service support.

The console of the present invention provides the ability for the user to read and display log files directly on the panel PC, improving serviceability and ease-of-use. The prior art has independent service software to extract and view the data logs.

Remote Control

Various timer controls found on the main console are duplicated on a hand-held remote control: site increment/decrement, cycle increment/decrement and timer start/stop and clear. Large blue buttons on a white background provide desired optical contrast and visibility in low light environments and good tactical feedback. Communication uses the IEEE 802.15.4 communication standard and chips in both the console and remote control contain a unique serial number that is used to establish a one-to-one connection.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed:

1. A mobile cryosurgical apparatus for cryogenic spray ablation comprising:
   a cryogen tank for storing cryogen under pressure;
   a cryogen pressure measuring device configured to measure a pressure of the cryogen tank;
   a cryogen pressure maintenance system configured to monitor a pressure of the cryogen tank via the cryogen pressure measuring device and control the pressure of the cryogen in the cryogen tank during use of the mobile cryosurgical apparatus;
   a cryogen level measuring device configured to measure a cryogen level in the cryogen tank;
   a cryogen tank fill system for filling the cryogen tank with cryogen;
   a catheter attachment apparatus for attaching a catheter to the mobile cryosurgical apparatus;
   a catheter pre-cool system for precooling the catheter;
   a catheter defrost system for defrosting the catheter;
   an on-board suction system configured to evacuate gas from a treatment area;
   a user-control system for user-control of cryogen flow and application of suction via the on-board suction system;
   an on-board computer screen for interacting with the mobile cryosurgical apparatus; and
   an on-board control system comprising a non-transitory computer readable medium containing computer readable instructions for: monitoring and adjusting cryogen pressure via the cryogen pressure maintenance system, controlling a cryogen tank fill operation via the cryogen tank fill system, running pre-procedure system checks, controlling catheter pre-cool and defrost using the catheter pre-cool system and the catheter defrost system, respectively, and controlling thermal, timing and suction functions at least in part using the user-control system during user treatment of patient;
   wherein said cryogen level measuring device comprises:
   a three-point cryogen tank support system;
   an electronic load cell located at one point of the three point cryogen tank support system and configured to determine the load borne by the support at one point;
   and electronics for communication the load recorded to the on-board control system.

2. The mobile cryosurgical apparatus according to claim 1, wherein said cryogen pressure measuring device comprises an electronic pressure sensor configured to monitor the pressure of the cryogen tank, and the cryogen pressure maintenance system comprises an electronic pressure build solenoid configured to respond to instructions from said on-board control system to selectively allow flow of liquid cryogen from a lower portion of said cryogen tank to an upper portion of said cryogen tank in order to increase the pressure thereof as necessary, and an electronic solenoid vent under control of said on-board control system to selectively vent cryogen from said cryogen tank to decrease the pressure thereof as necessary.

3. The mobile cryosurgical apparatus according to claim 1, wherein said cryogen tank fill system monitors a level of cryogen in the cryogen tank and sends instructions to an electronic cryogen fill solenoid to close off flow of cryogen into said cryogen tank and automatically vents a supply hose.

4. The mobile cryosurgical apparatus according to claim 1, further comprising a user input interface that permits the user to select the delivery of cryogen at a plurality of discrete pressures.

5. The mobile cryosurgical apparatus according to claim 1, further comprising a user input interface that permits the user to select the use of passive venting only, or active venting at a plurality of discrete suction powers.

6. The mobile cryosurgical apparatus according to claim 1, wherein the catheter pre-cool system may be set to automatic by the user and prevents the flow of cryogen into the catheter until cryogen delivery components internal to the cryosurgical apparatus reach a specified temperature.

7. The mobile cryosurgical apparatus according to claim 1, further comprising a cryosurgical catheter for delivering low pressure spray to a treatment area, in conjunction with an endoscope, comprising an inner tube of extruded polyimide, a layer of braided stainless steel over the extruded polyimide, and a layer of polyether block amide extruded over the braided stainless steel, wherein the polyether block amide extends through the stainless steel braid to at least partially contact the polyimide layer, said cryogen delivery catheter further comprising a blunted tip comprising polyether block amide; wherein said catheter is capable of retroflex during use, without delamination.

8. The cryosurgical system according to claim 1, further comprising:
   a cryogen delivery system including a cryogen tank lance in fluid communication with the cryogen tank for receiving liquid nitrogen from the cryogen tank;
   a cryogen valve in liquid communication with and downstream of the cryogen tank lance for controlling flow of cryogen from the lance to components located downstream from the lance;
   a manifold assembly in liquid communication with the cryogen valve, said manifold assembly comprising a manifold vent and also being in liquid communication and downstream from a defrost valve which selectively supplies warmed cryogen to said manifold; and
   a catheter valve in liquid communication with and downstream from said manifold assembly, for delivering cryogen to a cryosurgery catheter,
   wherein dimensions of said cryogen tank, said manifold assembly, said manifold vent, and said cryosurgery catheter are selected to dampen a dynamic response of the system during cryogen delivery.

9. The cryosurgical system according to claim 8 further comprising instructions for performing active feedback control.

* * * * *